United States Patent
Yomtov et al.

(10) Patent No.: US 8,663,202 B2
(45) Date of Patent: Mar. 4, 2014

(54) WIRELESS REMOTE NEUROSTIMULATOR

(75) Inventors: Barry Mitchell Yomtov, Marblehead, MA (US); John R. Batty, Miami, FL (US); Marvin L. Sussman, Miami, FL (US)

(73) Assignee: AdvaStim, Inc., Beverly, MA (US)

(*) Notice: Subject to any disclaimer, the term of this patent is extended or adjusted under 35 U.S.C. 154(b) by 0 days.

(21) Appl. No.: 13/472,430

(22) Filed: May 15, 2012

(65) Prior Publication Data

US 2012/0296271 A1    Nov. 22, 2012

Related U.S. Application Data

(60) Provisional application No. 61/488,303, filed on May 20, 2011.

(51) Int. Cl.
    *A61K 9/22*    (2006.01)
    *A61N 1/00*    (2006.01)

(52) U.S. Cl.
    USPC ............................ 604/891.1; 607/3; 607/60

(58) Field of Classification Search
    USPC ........... 604/890.1–891.1; 607/5–7, 60, 62, 72
    See application file for complete search history.

(56) References Cited

U.S. PATENT DOCUMENTS

| | | | |
|---|---|---|---|
| 7,599,737 B2 * | 10/2009 | Yomtov et al. | 607/3 |
| 7,917,208 B2 * | 3/2011 | Yomtov et al. | 607/3 |
| 2002/0072784 A1 * | 6/2002 | Sheppard et al. | 607/60 |
| 2002/0183686 A1 | 12/2002 | Darvish et al. | |
| 2004/0127942 A1 * | 7/2004 | Yomtov et al. | 607/3 |
| 2004/0204744 A1 * | 10/2004 | Penner et al. | 607/23 |
| 2006/0041276 A1 | 2/2006 | Chan | |
| 2006/0116611 A1 | 6/2006 | Richter | |
| 2007/0255323 A1 * | 11/2007 | Werder et al. | 607/3 |
| 2009/0024180 A1 * | 1/2009 | Kisker et al. | 607/32 |
| 2011/0046698 A1 * | 2/2011 | Kivi et al. | 607/60 |
| 2012/0221068 A1 * | 8/2012 | Ellingson | 607/17 |
| 2012/0265271 A1 * | 10/2012 | Goetz | 607/59 |
| 2012/0277817 A1 * | 11/2012 | Ellingson et al. | 607/25 |
| 2012/0277818 A1 * | 11/2012 | Stancer et al. | 607/32 |

OTHER PUBLICATIONS

International Search Report of Oct. 24, 2012 for PCT/US2012/038066, International filing date of May 16, 2012 for "Implantable Wireless Therapy System" 5 pages.

* cited by examiner

*Primary Examiner* — Quynh-Nhu H Vu
(74) *Attorney, Agent, or Firm* — Graybeal Jackson LLP (57) ABSTRACT

A therapy system includes a therapy module implantable within a mammalian body that provides a given therapy and a control module implantable within the mammalian body that effects the therapy provided by the therapy module. The control module is physically separate from the therapy module.

43 Claims, 6 Drawing Sheets

WIRELESS REMOTE NEUROSTIMULATOR

PRIORITY CLAIM

The present application claims the benefit of copending U.S. Provisional Patent Application Ser. No. 61/488,303 filed May 20, 2011, which application is incorporated herein by reference in its entirety.

BACKGROUND

The present invention generally relates to an implantable therapy system. The present invention more particularly relates to such a system wherein the administration of therapy is electronically controlled by a control module and wherein a therapy module that delivers a given therapy is physically separate from the control module.

Implantable therapy delivery systems have been in the art and in commercial use for decades. Such systems include cardiac rhythm management systems such pacemakers and defibrillators, nerve stimulators, and even drug delivery systems.

Such therapy systems, and especially in the case of cardiac rhythm management and nerve stimulator systems, include an implantable device that includes a power source, such as a battery and electronic circuitry that generates therapy stimulation pulses and controls when the therapy stimulation pulses are delivered. To actually deliver the stimulation pulses, the systems also generally include multiple stimulation electrodes on the surface of a lead that make electrical contact with the desired (target) tissue and a lead system, including one or more leads that connect the electrodes to the electronic circuitry in the device.

As implantable therapy device design has progressed over time, more and more functionality has been incorporated into the implantable devices and more and more electrodes have been similarly required to shape stimulation at the target tissue volume to enable that functionality. For example, implantable therapy devices usually now incorporate microcontrollers that are capable of controlling multiple therapy delivery modalities in multiple locations of the body. Those modalities may include both stimulation pulse delivery to selected tissue(s) and/or physiologic activity monitoring and data gathering for analysis and adjustment of therapy. In the case of nerve stimulation systems, these systems now find use in various locations of the body as for example, in brain tissue stimulation and spinal nerve stimulation.

Particularly in nerve stimulators, there has been an increase in the number of electrodes assigned to shape and deliver electrical pulses to a given anatomical region. The intended advantage is to obtain stimulation selectivity and directionality and to shape current delivery to a volume of tissue. Today, a system may incorporate as many as sixteen to twenty electrodes in a given area. Unfortunately, current state of the art connectivity measures to connect the electrodes back to the implantable pulse generation devices have limited the number and utility of electrodes.

For example, each electrode requires an electrical conductor or wire to extend from the electrode through its associated lead and back to the implanted device. The large number of such conductors is limited by the amount of space available in a lead. Further, each conductor requires a hermetically sealed connection with the implanted device. This places a huge burden on feed through systems which can accommodate only a limited number required contacts and in effect, limits the number of electrodes to the constraints imposed by the connector.

Still further, the required higher density of conductors required for the increased number of electrodes results in smaller diameter conductors. The smaller diameter conductors present higher impedance conduction paths between the electrodes and the implantable devices. This results in higher required power output from the implantable electronic devices to deliver the desired effective stimulation therapy. The required higher power output also either decreases battery life of the implantable devices or requires larger batteries to be employed. The smaller diameter conductor wire would also exhibit reduced strength and flex life in locations where this results in reduced reliability of the cable lead. Such stresses at the lead/stimulator connections cause an unacceptably high rate of device failure.

As a further matter, some clinical applications of nerve stimulators require the location of the electrodes to be in locations where replacement of the electrodes would require surgery and impose increased clinical risk to the patient. Also, anchoring the lead can be an issue to prevent the dislodgement of electrode(s) by inadvertent body movement or pulling on the lead. For example, anchoring leads at the exit of the vertebrae for spinal cord stimulation has been a reliability limitation of current technology.

As may be seen from the foregoing, there is a need in the art for a different approach in providing therapy within a body where a control device must be connected to monitoring and therapy delivery elements such as sensing or pulse delivery electrodes. It would be desirable if such an approach would avoid high impedance conduction paths, minimize electrode dislodgement, prevent interconnection issues and increase the safety to and convenience of the patient. The present invention addresses these and other issues.

SUMMARY

The invention provides a therapy system including a therapy module implantable within a mammalian body that provides a given therapy, and a control module implantable within the mammalian body that affects the therapy provided by the therapy module. The control module is physically separate from the therapy module.

The therapy module may be a drug delivery module, a stimulation pulse generation module, or a combination of the two. The therapy module may include a substantially planar member having a surface and a plurality of stimulation electrodes arrayed on the surface of the substantially planar member. The substantially planar member may be formed from flexible material.

The therapy module may include a substantially cylindrical member having a substantially cylindrical surface and a plurality of stimulation electrodes arrayed on the substantially cylindrical surface of the substantially cylindrical member. The substantially cylindrical member may be formed from flexible material. The plurality of electrodes may be ring electrodes or directional circular disk electrodes.

The therapy module may include a substantially planar member having a surface, a first plurality of stimulation electrodes arrayed on the surface of the substantially planar member, a substantially cylindrical member extending from the substantially planar member and having a substantially cylindrical surface, and a second plurality of stimulation electrodes arrayed on the substantially cylindrical surface of the substantially cylindrical member. The second plurality of electrodes may be ring electrodes or directional circular disk electrodes.

The system may further include a communication link between the therapy module and the control module. The communication link may be a near field communication link. The near field communication link may be a two-way communication link. The near field communication link may be an electromagnetic link. The near field electromagnetic link may include a first coil carried by the control module and a second coil carried by the therapy module.

The control module may provide the therapy module with at least one operating parameter over the communication link. The therapy module may include a processor that controls the provision of the given therapy in accordance with the at least one operating parameter.

The control module may include a receiver that receives the at least one operating parameter from an external programming source. The receiver may be an RF receiver.

The control module may include a transceiver that establishes a two-way communication link with the external programming source. The transceiver may be an RF transceiver.

The therapy module may be a stimulation pulse generation module. The at least one operating parameter may be stimulation pulse timing, stimulation pulse amplitude, or stimulation pulse duration. The therapy module may include a plurality of electrodes and the at least one operating parameter may also include electrode selection parameters.

The system may further include a power transmission link from the control module to the therapy module that enables the therapy module to be powered by the control module. The power transmission link may be a near field electromagnetic link. The power transmission near field electromagnetic link may include a first coil carried by the control module and a second coil carried by the therapy module and the communication near field electromagnetic link may include a third coil carried by the control module and a fourth coil carried by the therapy module. The first and third coils may be arranged side-by-side to each other and the second and fourth coils may be arranged side-by-side to each other. Alternatively, the first and third coils may be arranged with respect to each other such that the third coil is disposed concentric within the first coil.

The invention further provides a therapy system including a first therapy module implantable within a mammalian body that provides a first given therapy, and a second therapy module implantable within a mammalian body that provides a second given therapy. The system further includes a control module implantable within the mammalian body that affects the first and second therapy modules. The control module is physically separate from the first and second therapy modules.

At least one of the first and second therapy modules may be a drug delivery module. One of the first and second therapy modules may be a stimulation pulse generation module. Each of the first and second therapy modules may be a stimulation pulse generation module.

The system may further include a communication link between each of the first and second therapy modules and the control module. The communication link may be a near field communication link.

The control module may provide each of the therapy modules with at least one operating parameter over its respective communication link. Each of the therapy modules may include a microcontroller that controls the provision of its given therapy in accordance with at least one operating parameter.

The control module may include a receiver that receives the at least one operating parameter from an external programming source. The receiver may be an RF receiver.

The control module may include a transceiver that receives the at least one operating parameter from an external programming source. The transceiver may be an RF transceiver.

The system may further include a power transmission link from the control module to each of the first and second therapy modules that enable the therapy modules to be powered by the control module. The power transmission link may be a near field electromagnetic link. One of the therapy modules may be a sensing module that senses physiological data.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

DETAILED DESCRIPTION

Figure 1:
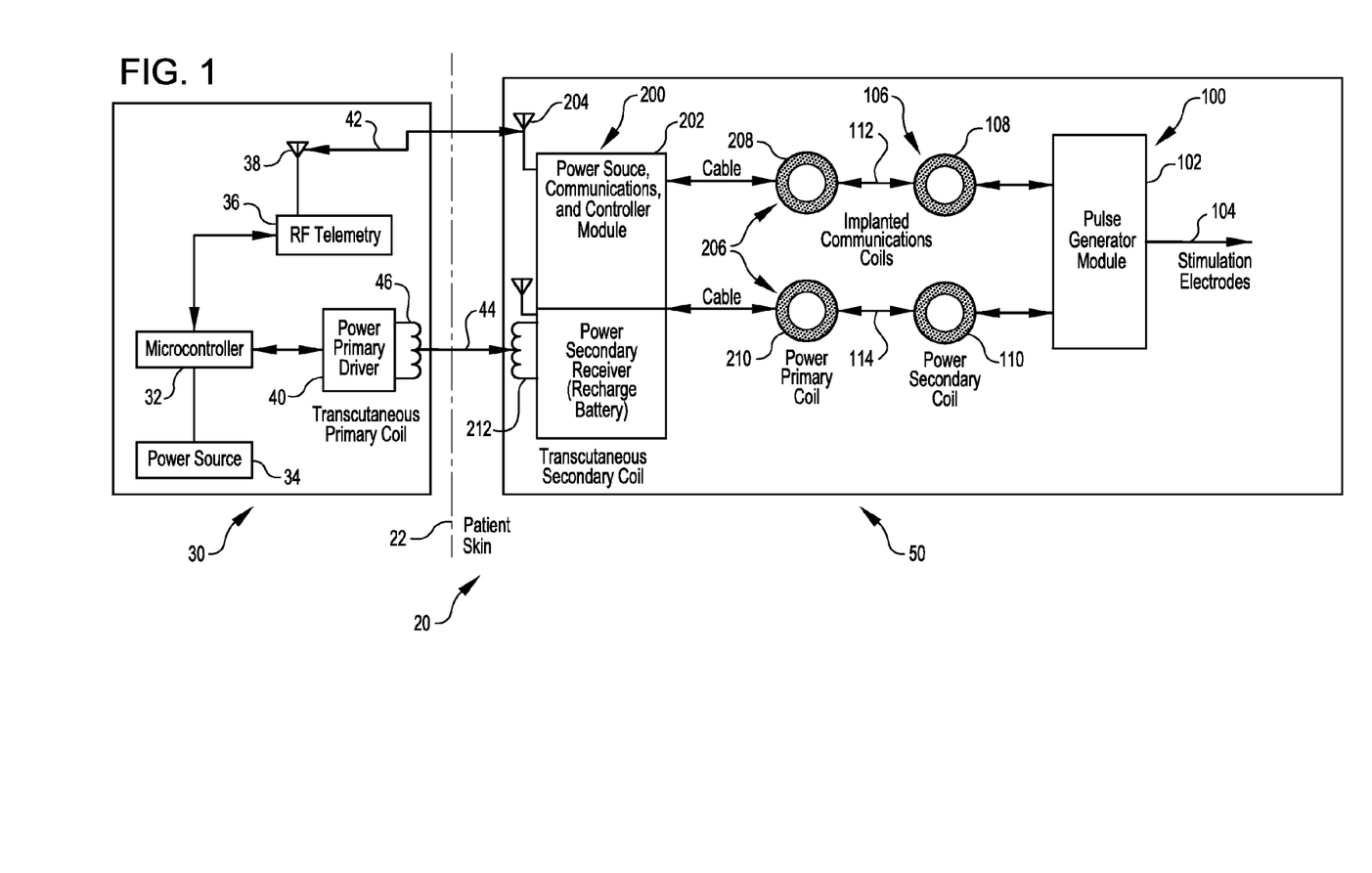
FIG. 1 is a simplified block diagram of a system according to one embodiment of the invention.

Referring now to FIG. 1, it is a simplified block diagram of a system 20 according to one embodiment of the invention. The system 20 generally includes an external programming and recharging instrument 30 and an implantable therapy system 50.

The implantable therapy system 50 includes a therapy module 100 and a control module 200 that are implantable beneath a patient's skin 22. The therapy module 100 is arranged to provide a given therapy and the control module 200 is arranged to affect the therapy provided by the therapy module 100. The control module 200 is physically separate from the therapy module 100.

As shall be seen subsequently, the therapy module 100 is arranged to provide a given therapy such as drug delivery therapy or stimulation pulse therapy, for example. To that end, the embodiment of FIG. 1 includes a pulse generator 102 having an output 104 that may be coupled to a plurality of stimulation electrodes in a manner to be described herein after. The therapy module 100 further includes a coil arrangement 106 including coils 108 and 110. Coil 108 forms a portion of an electromagnetic near field communication link 112 between the therapy module 100 and the control module 200. Coil 110 forms a portion of a power transmission link between the therapy module 100 and the control module 200.

The control module 200 includes circuitry 202 that provides control of the therapy module 100, that provides the therapy module 100 with sustaining power, and that communicates with and receives sustaining power from the external programming and recharging instrument 30. To support that functionality, the control module 200 includes an RF antenna 204 for communicating with the external instrument 30 through a two-way radio frequency (RF) far field communication link 42. The control module 200 further includes a coil arrangement 206 including coils 208 and 210. Coil 208 forms another portion of the electromagnetic near field communication link 112 between the therapy module 100 and the control module 200. Coil 210 forms another portion of the power transmission link 114 between the therapy module 100 and the control module 200. The control module 200 still further includes a secondary coil 212 that forms a portion of a second power transmission link 44 for receiving power from the external instrument 30 for recharging the implantable power source within the control module 200.

The communication link 112 between the control module 200 and the therapy module 100 is a two-way communication link. It enables operating parameters to be provided to the therapy module 100 from the control module 200. When the therapy provided by the therapy module 100 is electrical pulse neural stimulation, the operating parameters may include, for example, operating parameters for stimulation pulse timing, stimulation pulse amplitude, stimulation pulse duration, and/or electrode selection and polarity. The link 112 may also be used to control the power transfer between the control module 200 and the therapy module 100. The transmission carrier frequencies of the communication link 112 and the power transmission link 114 are preferably selected to be different by an order of magnitude to ensure there is no cross coupling of the power signal through the communication coils 208 and 108.

With continued reference to FIG. 1, the external instrument 30 includes a microcontroller that controls the function of the external instrument 30. The circuitry of the external instrument 30 is powered by a power source 34. The microcontroller 32 is coupled to an RF telemetry circuit 36 that includes an RF antenna 38 that completes the RF link 42 between the external instrument 30 and the control module 200. Lastly, the external instrument 30 includes a power driver 38 that through a coil 46 transfers battery charging power to the control module 200 over the second near field electromagnetic power transmission link 44.

The external instrument 30 is operated by a physician or other medical personnel to define the therapy operating parameters. The microcontroller 32 provides the control module 200 with all of the required operating parameters defining the given therapy delivered by the therapy module 100 over the RF communication link 42. Once the control module 200 has the operating parameters, it can then convey them to the therapy module 100 over the near field electromagnetic communication link 112 for execution. The therapy module 100 will execute the therapy delivery according to the operating parameters received from the control module 200 until it receives revised parameters from the control module 200. As a result, the therapy module 100, in terms of control, is a standalone unit, capable of delivering the given therapy without the further assistance from the control module 200 until the therapy module 100 receives revised parameters from the control module 200. Once such revised parameters are received, the therapy module 100 can then continue to provide the given therapy, but according to the now revised parameters. The foregoing continues with the ultimate control of the therapy parameters in the hands of the physician or medical personnel who operates the external instrument 30.

The therapy module 200 may allow the patient some limited control and selectivity of the operational therapy parameters. It may also upload data from the implanted system over the RF link 42 to the external instrument 30 for trans-telephonic or internet transfer to the physician's office or into electronic health or personal health records.

All the while that the therapy module 100 is providing the therapy, it is receiving sustaining power from the control module 200 over the near field electromagnetic link 114. Control and regulation of the power transfer can be carried out over the two-way near field electromagnetic communication link 112. When therapy is temporarily disabled (i.e. turned off), the power transfer from the control module 200 to the therapy module 100 is suspended. The therapy module 100 retains the previous set of operating parameters until the therapy is resumed.

Figure 2:
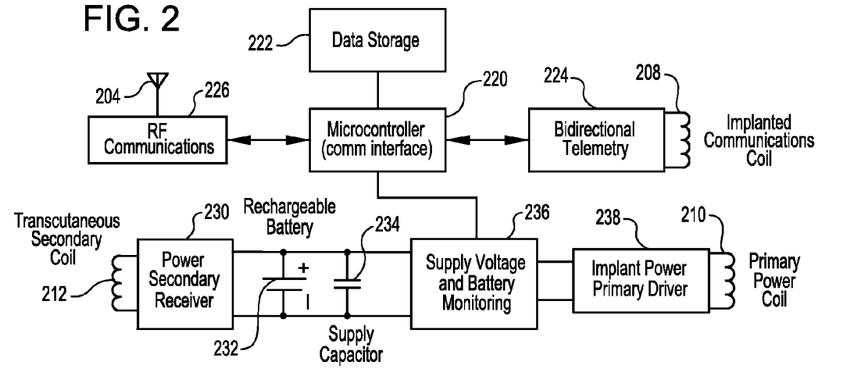
FIG. 2 is a block diagram of a control module that may be employed in the system of FIG. 1 according to an embodiment of the invention.

FIG. 2 is a more detailed block diagram of the control module 200 that may be employed in the system of FIG. 1 according to an embodiment of the invention. As may be noted in FIG. 2, the control module 200 further includes a microcontroller 220, data storage 222, a bidirectional telemetry circuit 224 and an RF communications circuit 226. The control module 200 still further includes a power secondary receiver 230, a rechargeable battery 232, a supply capacitor 234, a supply voltage and battery monitoring circuit 236, and an implant power primary driver 238.

The microcontroller 220 controls the overall functioning of the control module 200. It is coupled to the data storage 222 that stores data, such as the operating parameters received from the external instrument 30 (FIG. 1) diagnostic data collected by the implanted system 50 to be transferred to the external instrument 30, along with operating instruction for the microcontroller 220. The RF communications circuit 226 is preferably a transceiver, containing both an RF transmitter and an RF receiver, as is known in the art. The bidirectional telemetry circuit 224 is coupled to the communications coil 208 and is also preferably a transceiver to support the two-way communications between the control module 200 and the therapy module 100.

The power secondary receiver 230 receives battery recharging power from the external instrument 30. The received power is used to charge the rechargeable battery 232. Part of the stored energy is used to power the control module 200. Another portion of the stored power is transmitted to the therapy module 100 by the implant power primary driver 238 and the power transmission coil 210. Because the communication link provided by coil 208 and the power transmission link provided by coil 210 are near field, they will not interfere with the far field RF transmission link provided by antenna 204 and communications circuit 226.

Figure 3:
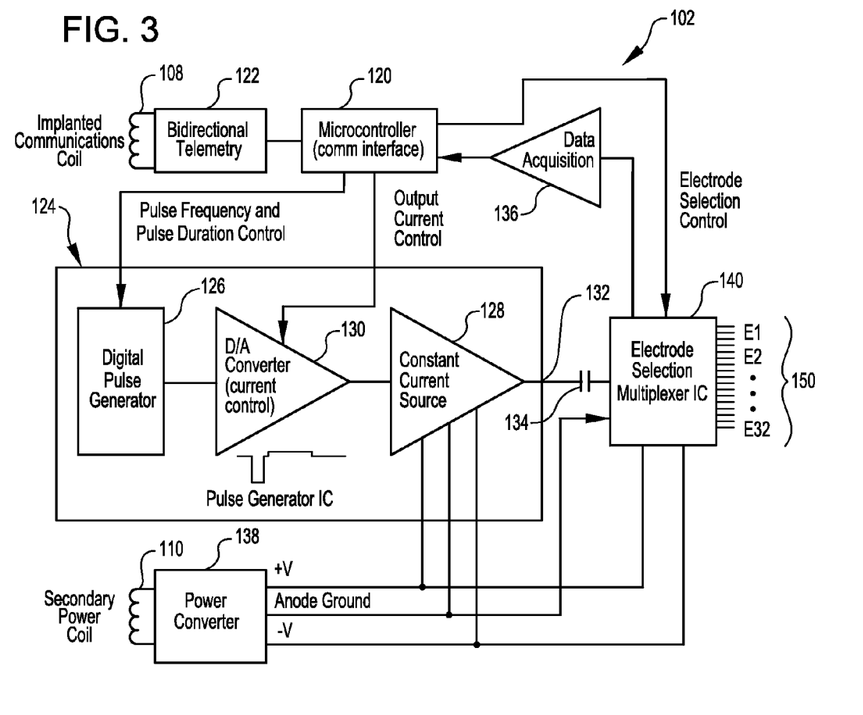
FIG. 3 is a block diagram of a pulse generator module that may be employed in the system of FIG. 1 according to an embodiment of the invention.

FIG. 3 is a block diagram of the circuit for the pulse generator module 102 of the therapy module 100 that may be employed in the system of FIG. 1. The pulse generator module 102 includes a microcontroller 120 that controls the functioning of the pulse generator circuit 102. It is coupled to the communication coil 108 by a bidirectional telemetry circuit 122. This supports both receipt of incoming data, such as programming data from the control module 200 and transmission of outgoing data, such as sensed diagnostic data, to the control module 200.

The pulse generator module 102 further includes a pulse generator circuit 124 that includes a digital pulse generator 126, a D/A converter 130, and a constant current source 128. The digital pulse generator 126 generates the pulse train and receives input from the microcontroller 120 to determine the stimulation pulse characteristics such as, for example, pulse frequency and pulse duration. The D/A converter 130 also receives input from the microcontroller 120 to determine the amplitude of the pulses. The output 132 of the pulse generator circuit 124 is coupled through capacitor 134 to an electrode selection multiplexer circuit (MUX) 140. The MUX 140 is coupled to an array of electrodes by outputs 150 and to the microcontroller 120 which controls the electrode selection.

As may be further noted in FIG. 3, a data acquisition circuit 136 is coupled from the MUX 140 to the microcontroller 120. This supports the transmission of diagnostic data back to the control module 200. The electrode selection provided by the MUX 140 may thus provide electrode selection for stimulation, patient ground, or data acquisition.

Lastly, the pulse generator module 102 includes a power converter 138 that is coupled to power transmission coil 110. The power converter 138 converts the power received over the power transmission link 114 to a form useful by the circuits and provides all of the circuit elements within the therapy module 100 with sustaining power.

As previously mentioned, the pulse characteristics are set by the control module 200 and are transmitted to the microcontroller 120 for execution. The pulse generator module 102 will continue to provide the pulses with those characteristics on its own until they are changed by the control module 200.

Figure 4:
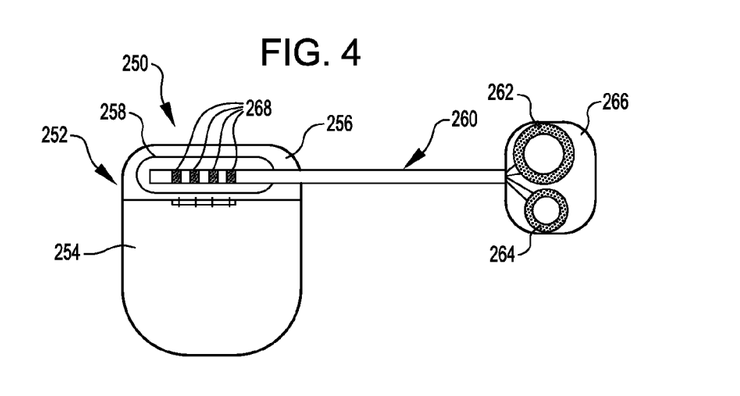
FIG. 4 is a side plan view of a control module according to an embodiment of the invention.

FIG. 4 is a side plan view of a control module 250 embodying the invention. The circuitry of the control module 250 is housed within a hermetically sealed enclosure 252. The enclosure 252 may have a body portion 254 formed from, for example, titanium. The enclosure may also include a header portion 256 which may be formed from plastic. The header 256 may be secured to the body 254 in a manner known in the art. Within the header 256 is the RF antenna 258 which may be used to support communication with an external programming instrument 30 like that shown in FIG. 1.

The control module 250 further includes a cable 260 that couples the circuits within the enclosure 252 to a near field electromagnetic power transmission coil 262 and to a near field electromagnetic communication coil 264. The coils 262 and 264 are carried on a base or substrate 266. At the end of the cable 260 opposite the coils 262 and 264, the cable includes contacts 268. The contacts serve to connect the coils to the circuitry within the body 254 of the enclosure 252.

In use, the therapy module 100 is implanted beneath the patient's skin and close to the target tissue to be stimulated. The base 266 for the coils 262 and 264 is placed in close proximity to the corresponding coils of the therapy module 100 as, for example, schematically shown in FIG. 1.

Figure 5:
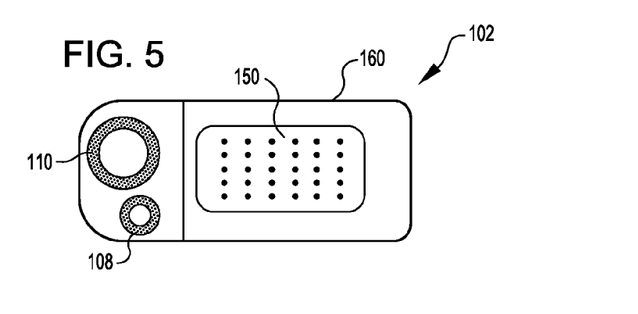
FIG. 5 is a top plan view of a pulse generator module according to an embodiment of the invention.

FIG. 5 is a top plan view of the pulse generator module 102 according to an embodiment of the invention. The pulse generator module 102 is a hermetically sealed device which houses the pulse generator circuits and electronic control functions for the device. To that end, the pulse generator module 102 includes a hermetic enclosure 160 that may be formed from titanium or ceramic materials, for example. The enclosure 160 houses the near field electromagnetic coils 108 and 110. It also includes a plurality of outputs 150 for connecting the circuits within the enclosure 160 to the plurality of electrodes.

Figure 6:
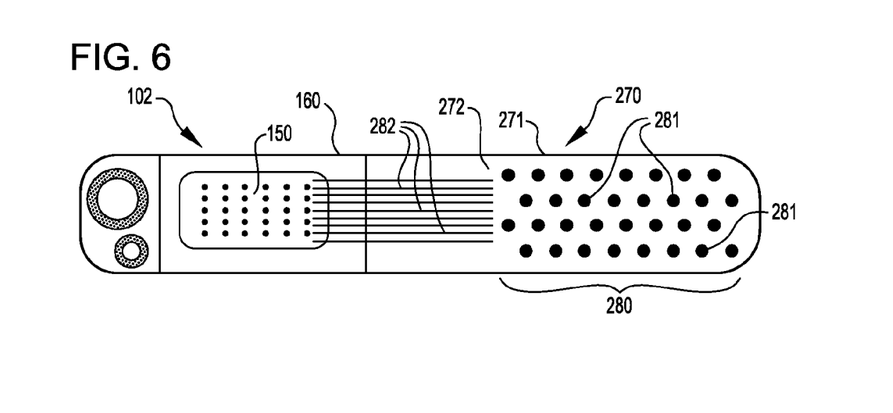
FIG. 6 is a top plan view of an electrical pulse stimulation therapy module according to an embodiment of the invention.

FIG. 6 illustrates a therapy module 270 employing the pulse generator module 102. The enclosure 160 is secured to a thin film electrode array 280 in the form of substantially planar substrate 271 having a substantially planar surface 272. Upon the surface 272 is an array 280 of a plurality electrodes 281. The electrodes 281 are directional circular disk electrodes. The electrodes may take many different shapes as is known in the art. Selected ones of the electrodes 281 of the electrode array 280 are coupled to selected ones of the outputs 150 of the pulse generator module 102 by conductors 282. The conductors 282 may be formed using thin film techniques known in the art. The substrate 271 may have a silicone backing to the thin film array to add strength and structure to the thin film component. Once the therapy module 270 is secured with an anchor (not shown), there is no lead cable that must exit anatomical structure, such as vertebrae, to the pulse generator module 102. Hence, the pulse generator module 102 and electrode array 280 will have no mechanical lead connection and thus no forces would be exerted from an exiting catheter which historically has dislodged electrodes.

Figure 7:
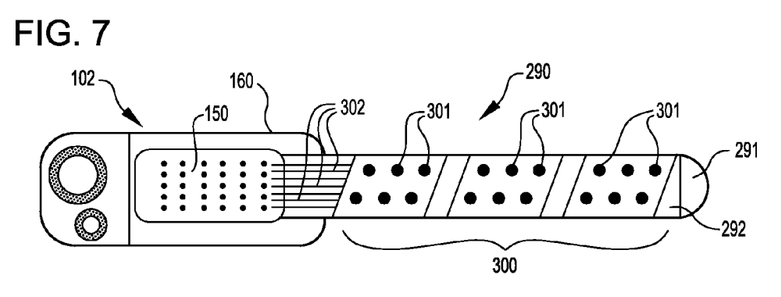
FIG. 7 is a top plan view of another electrical pulse stimulation therapy module according to an embodiment of the invention.

FIG. 7 illustrates another therapy module 290 employing the pulse generator module 102. The enclosure 160 is secured to a thin film electrode array 300 of directional circular disk electrodes 301 that is wrapped about a substantially cylindrical member 291 having a substantially cylinder surface 292. This forms a therapy module 290 that is configured as a catheter design.

The cylindrical member 291 may be a silicone rod, for example. Upon the cylindrical surface 292 are arrayed the plurality electrodes 301. Selected ones of the electrodes 301 of the electrode array 300 are coupled to selected ones of the outputs 150 of the pulse generator module 102 by conductors 302. The conductors 302 may be formed using thin film techniques known in the art. The wrapping of the thin film electrode array 300 around the silicone rod provides improved reliability and stability in the targeted neural tissue. This design configuration would provide clinical benefits for spinal cord stimulation and deep brain stimulation with a small diameter catheter along with electrodes that are directional.

Figure 8:
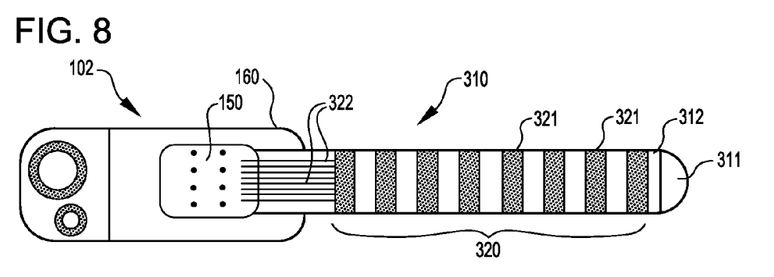
FIG. 8 is a top plan view of another electrical pulse stimulation therapy module according to an embodiment of the invention.

FIG. 8 illustrates another therapy module 310 employing the pulse generator module 102 and wherein the electrodes 321 are arrayed on a substantially cylindrical surface 312. To that end, the enclosure 160 is secured to an electrode array 320 of electrodes 321 that is wrapped about a substantially cylindrical member 311 having a substantially cylinder surface 312. Here, however, the electrodes 321 take the form of ring electrodes. This again forms a therapy module 310 that is configured as a catheter design. The cylindrical member 311 may again be a silicone rod, for example. Selected ones of the electrodes 321 of the electrode array 320 are coupled to selected ones of the outputs 150 of the pulse generator module 102 by conductors 322. The conductors 322 may be formed using conductive wire techniques known in the art. The embodiment of FIG. 8 also provides improved reliability and stability in the targeted neural tissue. This design configuration would provide clinical benefits wherever a small diameter catheter is needed along with electrodes that propagate energy in a radial pattern.

Figure 9:
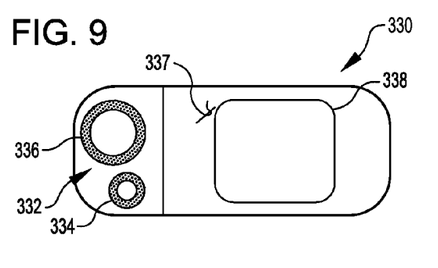
FIG. 9 is a top plan view of a drug delivery therapy module according to an embodiment of the invention.

FIG. 9 shows another therapy module 330 according to a further embodiment of the invention. Here, the therapy module 330 is a drug delivery therapy module. The drug delivery therapy module may take the form of the drug delivery device described, for example, in U.S. Pat. No. 7,599,737 entitled MEDICAL DEVICE FOR NEURAL STIMULATION AND DRUG DELIVERY, the disclosure of which patent is incorporated herein by reference in its entirety. As in the previous embodiments, the therapy module 330 includes an antenna arrangement 332 that may include a near field communications coil 334 and a near field power transmission coil 336. The drug delivery device 336 may be housed within a hermetic enclosure 338 along with the communications and power reception circuitry of the therapy module 330.

Figure 10:
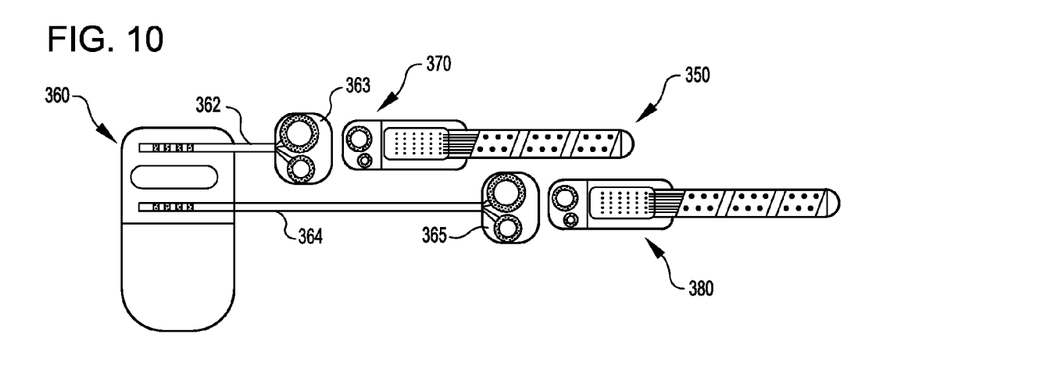
FIG. 10 is a plan view of an implantable therapy system according to a further embodiment of the invention which includes two electrical pulse stimulation modules.
Figure 11:
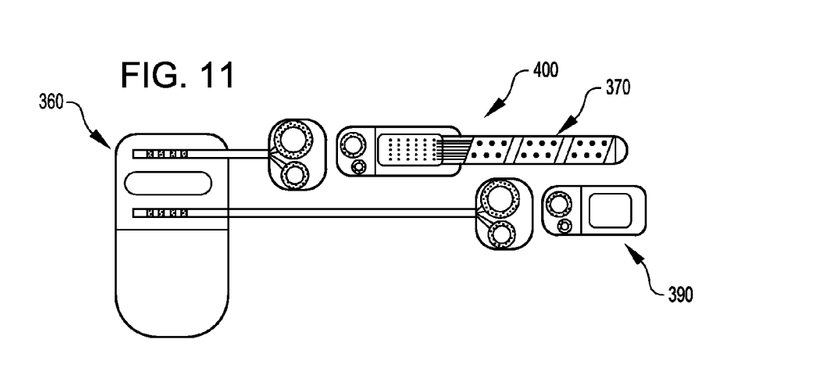
FIG. 11 is a plan view of an implantable therapy system according to a further embodiment of the invention which includes an electrical pulse stimulation module and a drug delivery therapy module.

Referring now to FIG. 10, it is a plan view of an implantable therapy system 350 according to a further embodiment of the invention which includes two electrical pulse stimulation modules. In practice, any number of therapy modules may be employed with a control module 360 having the requisite number of near field coil arrangements to support power transfer to and control of each therapy module employed. Here in FIG. 10, a control module 360 controls and supports a pair of electrical pulse stimulation modules 370 and 380. The electrical pulse stimulation modules 370 and 380 may take the form of the electrical pulse stimulation module 290 of FIG. 7 and the control module 360 may take the form of the control module 250 of FIG. 4. Here however, the control module 360 includes a pair of cables 362 and 364 each terminating in a coil arrangement 363 and 365 respectively so that both therapy modules 370 and 380 may be controlled and powered. With more than one therapy module, the control module 360 would interface with all therapy modules in determining which therapy module should be providing therapy at any given time, in synchronizing therapy delivery, and in providing operating parameters to each therapy module as required. Of course, the various therapy modules could be, for example, neurostimulators, drug delivery devices, or sensing modules for sensing physiological signals indicative of, for example, intracranial pressure or evoked potentials. For example, FIG. 11 shows a system 400 including control module 360 along with an electrical pulse stimulation module 370 and a drug delivery therapy module 390. Further, both therapy modules may be a drug delivery module.

Figure 12:
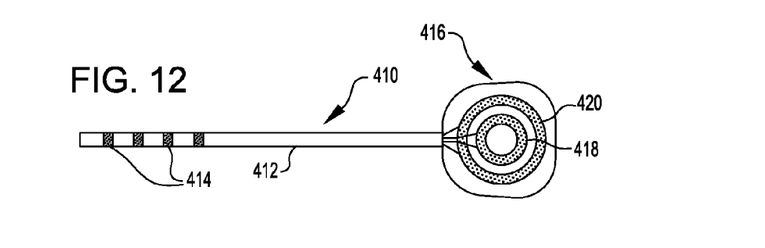
FIG. 12 is a top plan view of an alternative coil arrangement that may be used in a control module according to an embodiment of the invention.

FIG. 4 illustrates one cable and coil arrangement that may be used in a control module 200 according to an embodiment of the invention. FIG. 12, to which attention is now directed, shows an alternative cable and coil arrangement. The cable arrangement 410 shown in FIG. 12, like the arrangement of FIG. 4, includes a cable 412 having at one end a plurality of contacts 414 for being received within a header 256 of a control module enclosure 252. The other end of the cable 412 terminates in a coil arrangement 416 including coil 418 and coil 420. As may be noted, coil 418 is concentric within coil 420. This is in contrast to the side by side coil arrangement of FIG. 4.

Coil 420 may be used for power transfer while coil 418 may be used for communications. The coil within a coil arrangement of FIG. 12 occupies less space than the side by side coil arrangement of FIG. 4. Hence, the arrangement of FIG. 12 may be advantageous where space is a primary concern.

Figure 13:
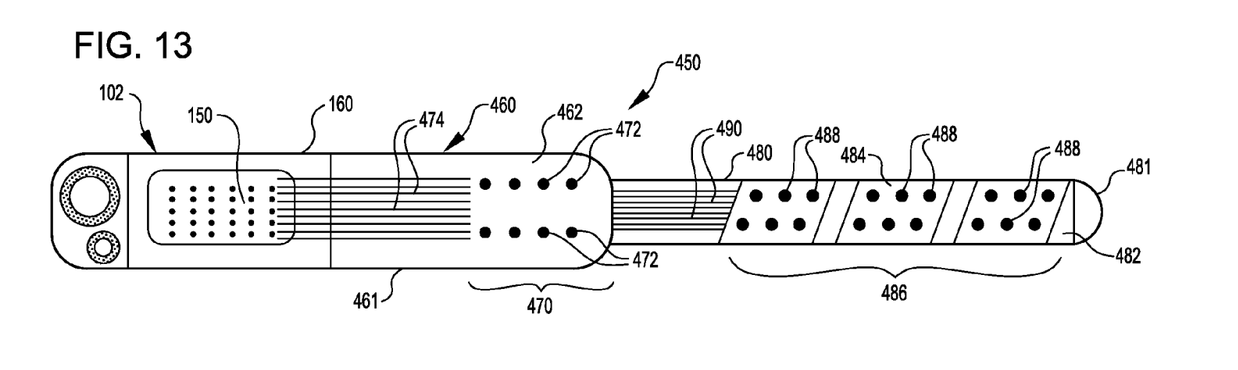
FIG. 13 is a top plan view of another electrical pulse stimulation therapy module according to an embodiment of the invention.

FIG. 13 shows a still further implantable therapy module embodying the invention. Here, the therapy module 450 is a combination planar surface electrode array and catheter type therapy module. As in previous embodiments, the therapy module 450 includes the pulse generator module 102. The enclosure 160 is secured to a thin film electrode array 460 in the form of substantially planar substrate 461 having a substantially planar surface 462. Upon the surface 462 is a first array 470 of a plurality of directional circular disk electrodes 472. Selected ones of the first plurality of electrodes 472 of the electrode array 470 are coupled to selected ones of the outputs 150 of the pulse generator module 102 by a first plurality of conductors 474. The conductors 474 may be formed using thin film techniques known in the art. The planar substrate 461 may have a silicone backing to the thin film array to add strength and structure to the thin film component.

Figure 14:
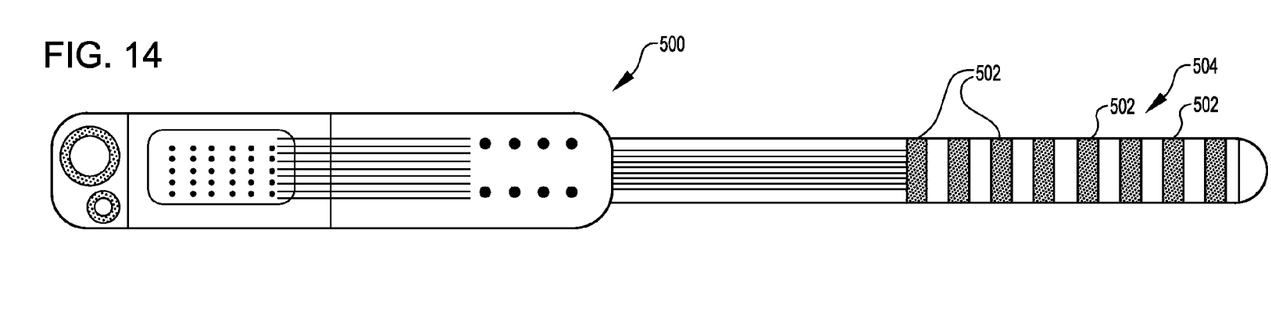
FIG. 14 is a top plan view of still another electrical pulse stimulation therapy module according to an embodiment of the invention.

Therapy module 450 further includes a cylindrical member 480 extending from the planar substrate 461. The cylindrical member 481 has a substantially cylindrical surface 482 upon which is wrapped a thin film 484 which carries a second electrode array 486 including a second plurality of directional circular disk electrodes 488. Selected ones of the outputs 150 are also coupled to selected ones of the second plurality of electrodes 488 by a second plurality of conductors 490. As a result, the therapy module 450 provides both a planar directional electrode array 470 and a catheter electrode array 486. This allows, for example, a lumbar or lower thoracic implantation of the therapy module 450 with the planar directional type electrodes 472, but also with the ability to place electrodes in the smaller upper thoracic region. FIG. 14 shows a similar arrangement. However in FIG. 14, the second plurality of electrodes 502 carried on the catheter portion 504 are ring electrodes.

While particular embodiments of the present invention have been shown and described, modifications may be made, and it is therefore intended in the appended claims to cover all such changes and modifications which fall within the true spirit and scope of the invention as defined by those claims.

What is claimed is:

1. A therapy system comprising:
a therapy module implantable within a mammalian body that provides a given therapy, the therapy module being without its own source of operating power;
a control module implantable within the mammalian body that effects the therapy provided by the therapy module, the control module being physically separate from the therapy module and including a power source; and
a wireless transmission link from the control module to the therapy module,
wherein, the control module is arranged to provide the therapy module with operating power over the wireless power transmission link only when the therapy module is providing the given therapy.

2. The system of claim 1, wherein the therapy module is a drug delivery module.

3. The system of claim 1, wherein the therapy module is a stimulation pulse generation module.

4. The system of claim 3, wherein the therapy module includes a substantially planar member having a surface, wherein the therapy module includes a plurality of stimulation electrodes, and wherein the plurality of electrodes are arrayed on the surface of the substantially planar member.

5. The system of claim 4, wherein the substantially planar member is formed from flexible material.

6. The system of claim 3, wherein the therapy module includes a substantially cylindrical member having a substantially cylindrical surface, wherein the therapy module includes a plurality of stimulation electrodes, and wherein the plurality of electrodes are arrayed on the substantially cylindrical surface of the substantially cylindrical member.

7. The system of claim 6, wherein the substantially cylindrical member is formed from flexible material.

8. The system of claim 6, wherein the plurality of electrodes includes ring electrodes or directional circular disk electrodes.

9. The system of claim 3, wherein the therapy module includes a substantially planar member having a surface, wherein the therapy module includes a first plurality of stimulation electrodes, wherein the first plurality of electrodes are arrayed on the surface of the substantially planar member, wherein the therapy module further includes a substantially cylindrical member extending from the substantially planar member and having a substantially cylindrical surface, wherein the therapy module includes a second plurality of stimulation electrodes, and wherein the second plurality of electrodes are arrayed on the substantially cylindrical surface of the substantially cylindrical member.

10. The system of claim 9, wherein the second plurality of electrodes includes ring electrodes or directional circular ring electrodes.

11. The system of claim 1, further including a communication link between the therapy module and the control module.

12. The system of claim 11, wherein the communication link between the therapy module and the control module is a two-way communication link.

13. The system of claim 11, wherein the control module provides the therapy module with at least one operating parameter over the communication link and wherein the therapy module includes a microcontroller that controls the provision of the given therapy in accordance with the at least one operating parameter.

14. The system of claim 13, wherein the control module includes a receiver that receives the at least one operating parameter from an external programming source.

15. The system of claim 14, wherein the receiver is an RF receiver.

16. The system of claim 13, wherein the therapy module is a stimulation pulse generation module, and wherein the at least one operating parameter is stimulation pulse timing, stimulation pulse amplitude, or stimulation pulse duration.

17. The system of claim 16, wherein the therapy module includes a plurality of stimulation electrodes, and wherein the at least one operating parameter also includes electrode selection parameters.

18. The system of claim 11, wherein the communication link is a near field communication link.

19. The system of claim 18, wherein the communication link is a near field electromagnetic link.

20. The system of claim 19, wherein the near field electromagnetic link includes a first coil carried by the control module and a second coil carried by the therapy module.

21. The system of claim 1, wherein the control module includes a transceiver that establishes a two-way communication link with an external programming source.

22. The system of claim 21, wherein the transceiver is an RF transceiver.

23. The system of claim 1, wherein the power transmission link is a near field electromagnetic link.

24. The system of claim 23, wherein the power transmission near field electromagnetic link includes a first coil carried by the control module and a second coil carried by the therapy module.

25. The system of claim 24, further including a communication near field electromagnet link between the control module and the therapy module including a third coil carried by the control module and a fourth coil carried by the therapy module.

26. The system of claim 25, wherein the first and third coils are arranged side-by-side to each other and wherein the second and fourth coils are arranged side-by-side to each other.

27. The system of claim 25, wherein the first and third coils are arranged with respect to each other such that the third coil is disposed concentric within the first coil.

28. A therapy system comprising:
   a first therapy module implantable within a mammalian body that provides a first given therapy;
   a second therapy module implantable within the mammalian body that provides a second given therapy,
   the first and second therapy modules being without their own source of operating power;
   a control module implantable within the mammalian body that effects the first and second therapies provided by the first and second therapy modules, the control module being physically separate from the first and second therapy modules and including an independent power source; and
   a wireless power transmission link from the control module to each of the first and second therapy modules,
   wherein, the control module is arranged to provide the first and second therapy modules with operating power over the wireless power transmission link.

29. The system of claim 28, wherein at least one of the first and second therapy modules is a drug delivery module.

30. The system of claim 29, wherein one of the first and second therapy modules is a stimulation pulse generation module.

31. The system of claim 28, wherein each of the first and second therapy modules is a stimulation pulse generation module.

32. The system of claim 28, wherein the first therapy module is a stimulation pulse generation module and the second therapy module is a drug delivery module.

33. The system of claim 28, further including a communication link between each of the first and second therapy modules and the control module.

34. The system of claim 33, wherein the control module provides each of the therapy modules with at least one operating parameter over its respective communication link and wherein the therapy modules each includes a microcontroller that controls the provision of its given therapy in accordance with its at least one operating parameter.

35. The system of claim 34, wherein the communication link is a near field communication link.

36. The system of claim 30, wherein the control module includes a receiver that receives the at least one operating parameter from an external programming source.

37. The system of claim 36, wherein the receiver is an RF receiver.

38. The system of claim 28, wherein the power transmission link is a near field electromagnetic link.

39. The system of claim 28, wherein the control module includes a transceiver that establishes a two-way communication link with an external programming source.

40. The system of claim 39, wherein the transceiver is an RF transceiver.

41. The system of claim 28, wherein at least one therapy module is a sensing module that senses physiological data.

42. The system of claim 1, further comprising a communication link between the control module and the therapy module that controls power transfer from the control module to the therapy module.

43. The system of claim 28, further comprising a communication link between the control module and the first and second therapy modules that controls power transfer from the control module to the first and second therapy modules.

* * * * *